(12) United States Patent
Herbst et al.

(10) Patent No.: US 11,666,292 B2
(45) Date of Patent: Jun. 6, 2023

(54) METHOD FOR MAKING AN EXPANDED X-RAY RECORDING

(71) Applicant: Siemens Healthcare GmbH, Erlangen (DE)

(72) Inventors: Magdalena Herbst, Pinzberg (DE); Ludwig Ritschl, Buttenheim (DE); Marc Cottiati, Zurich (CH); Christoph Luckner, Erlangen (DE); Qi Hu, Erlangen (DE); Marcel Beister, Erlangen (DE); Fabian Wloka, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 37 days.

(21) Appl. No.: 17/215,059

(22) Filed: Mar. 29, 2021

(65) Prior Publication Data

US 2021/0298699 A1    Sep. 30, 2021

(30) Foreign Application Priority Data

Mar. 31, 2020    (DE) .................... 10 2020 204 172.5

(51) Int. Cl.
*A61B 6/00*    (2006.01)

(52) U.S. Cl.
CPC .............. *A61B 6/40* (2013.01); *A61B 6/4452* (2013.01); *A61B 6/542* (2013.01); *A61B 6/4458* (2013.01)

(58) Field of Classification Search
CPC ......... A61B 6/40; A61B 6/4458; A61B 6/542; A61B 6/4452; A61B 6/5241; A61B 6/5235; A61B 6/5229
See application file for complete search history.

(56) References Cited

U.S. PATENT DOCUMENTS 8,867,700 B2 * 10/2014 Carton ..................... G21K 1/10
378/98.12
10,045,746 B2 * 8/2018 Tajima ................ A61B 6/4233
(Continued)

FOREIGN PATENT DOCUMENTS

EP          2517628 A1    10/2012
JP       2011019801 A      2/2011
JP       2011019801 A  *   2/2011

OTHER PUBLICATIONS

English Translation of JP-2011019801 (Year: 2011).*
(Continued)

*Primary Examiner* — Dani Fox
*Assistant Examiner* — Soorena Kefayati
(74) *Attorney, Agent, or Firm* — Harness, Dickey & Pierce, P.L.C.

(57) ABSTRACT

A method is for making an X-ray recording of an examination region of an examination object with an X-ray system including an X-ray source arranged on an emitter displacement unit and an X-ray detector including a detection area, arranged on a detector displacement unit. The method includes selecting the examination region and portion-wise recording successive recording portions in relation to the examination region. The portion-wise recording includes moving the X-ray source and the X-ray detector, determining a strip-shaped detection region within the detection area, by expanding an extent of the X-ray recording compared with a further different X-ray recording, and acquiring and recording each respective successive recording portion, of the successive recording portions, using the determined detection region and the X-ray source. Finally, the method includes generating an assembled X-ray recording of the examination region from the successive recording portions recorded.

19 Claims, 12 Drawing Sheets

(56) References Cited

U.S. PATENT DOCUMENTS

| | | | | |
|---|---|---|---|---|
| 2009/0046906 | A1* | 2/2009 | Wohlgemuth | A61B 6/4476 382/128 |
| 2009/0103679 | A1* | 4/2009 | Jabri | A61B 6/06 378/70 |
| 2010/0189214 | A1* | 7/2010 | Shibata | A61B 6/027 378/21 |
| 2010/0239145 | A1* | 9/2010 | Fujita | A61B 6/585 378/62 |
| 2010/0272236 | A1* | 10/2010 | Hirooka | A61B 6/5252 378/154 |
| 2011/0206185 | A1* | 8/2011 | Sakai | A61B 6/06 378/62 |
| 2012/0128119 | A1* | 5/2012 | Notohara | A61B 6/025 378/10 |
| 2012/0140877 | A1* | 6/2012 | Notohara | A61B 6/5241 378/22 |
| 2012/0275563 | A1* | 11/2012 | Manak | A61B 6/00 378/62 |
| 2013/0148779 | A1* | 6/2013 | Notohara | A61B 6/025 378/22 |
| 2014/0254753 | A1* | 9/2014 | Yamashita | A61B 6/06 378/62 |
| 2015/0250441 | A1* | 9/2015 | Okuno | A61B 6/547 378/62 |
| 2016/0113601 | A1* | 4/2016 | Notohara | A61B 6/5205 378/7 |
| 2016/0228086 | A1* | 8/2016 | Toyoda | A61B 6/463 |
| 2017/0135658 | A1* | 5/2017 | Saito | A61B 6/5235 |
| 2018/0049711 | A1* | 2/2018 | Ji | A61B 6/545 |
| 2019/0142356 | A1* | 5/2019 | Nakaya | A61B 6/00 378/98.8 |

OTHER PUBLICATIONS

Luckner, C. et. al., "Assessment of Measurement Deviations: Length-extended X-ray Imaging for Orthopedic Applications", SPIE Medical Imaging, 2019, California, United States, 2019.

Luckner Christph et al. "Parallel-Shift Tomosynthesis for Orthopedic Applications" Proc. SPIE 10573, Medical Imaging 2018: Physics of Medical Imaging, 105730G (Mar. 9, 2018); https://doi.org/10.1117/12.2292384.

Luckner, C. et al., "Towards full-body X-ray images", Bildverarbeitung für die Medizin 2018. Springer Vieweg, Berlin, Heidelberg, pp. 86-91, 2018.

German Office Action dated Jan. 15, 2021.

* cited by examiner

METHOD FOR MAKING AN EXPANDED X-RAY RECORDING

PRIORITY STATEMENT

The present application hereby claims priority under 35 U.S.C. § 119 to German patent application number DE 102020204172.5 filed Mar. 31, 2020, the entire contents of which are hereby incorporated herein by reference.

FIELD

Example embodiments of the invention generally relate to a method for making an X-ray recording, wherein the X-ray recording is assembled from strip-shaped recording portions; and to a medical X-ray system therefor.

BACKGROUND

In an X-ray recording assembled from a plurality of strip-shaped recording portions, a so-called slot-scan, the image field is limited by the detector size with regard to the width of the X-ray recording or the image, and the travel range of the X-ray system with regard to the height of the X-ray recording or the image. In robotic radiography systems, for example, the detector stand and/or the detector displacement unit can have a more restricted travel range.

Such X-ray recordings are known, for example, from Luckner, Christoph, et al. "Parallel-shift tomosynthesis for orthopedic applications." Medical Imaging 2018: Physics of Medical Imaging. Vol. 10573. International Society for Optics and Photonics, 2018 and from Luckner, Christoph, et al. "Towards Full-body X-ray Images.", Bildverarbeitung für die Medizin 2018. Springer Vieweg, Berlin, Heidelberg, 2018. 86-91.

SUMMARY

The inventors have recognized the problem that the width and/or the height of the X-ray recording or of the examination region can be insufficient for the examination. In some cases, the width of the X-ray recording can be insufficient to image, for example, a complete hip. A radiography system, in particular, a robotic system has a detector width of, for example, approximately 42 cm, and at an X-ray focus to X-ray detector spacing of, for example, 132 cm and an X-ray focus to examination object spacing of, for example, 105 cm this results in an image width in the object of approximately 33.4 cm. This is not sufficient for some applications or some examinations. In addition, it is desirable that the height of the X-ray recording can be as large as possible in order to be able to make whole body recordings of large examination objects or patients.

The inventors have also recognized that with an X-ray recording assembled from a plurality of strip-shaped recording portions, a so-called slot-scan, only a small constant region of the detection area of the X-ray detector, for example, approximately 5 cm of the height of the detection region is constantly used in the scanning direction or recording direction. If many such X-ray recordings are carried out one after another, a so-called bright-burn effect can come about. In this case, the detection region used during the recording becomes effectively burned in and is visible as a shadow if, in particular, subsequently an X-ray recording different therefrom is made in which the whole detection region is used.

In conventional X-ray recordings, typically the detector surface can be maximally utilized in that the magnification factor is kept as small as possible, that is, a smaller spacing between the examination object and the X-ray detector and a larger spacing between the X-ray source and the X-ray detector are selected.

Embodiments of the invention provide a method for making an X-ray recording of an examination region and a medical X-ray system as well as a computer program product and a computer readable medium, which enable an enlargement of the X-ray recording or of the examination region.

Embodiments of the invention are directed to a method for making an X-ray recording of an examination region, a medical X-ray system, a computer program product and a computer-readable medium.

At least one embodiment of the invention relates to a method for making a, particularly two-dimensional, X-ray recording of an examination region of an examination object with an X-ray system which comprises an X-ray source arranged on an emitter displacement unit and an X-ray detector with a detection area arranged on a detector displacement unit. The X-ray source can emit, in particular, X-ray radiation in the direction of the X-ray detector. The examination object is arranged between the X-ray source and the X-ray detector.

At least one embodiment of the invention relates to an X-ray system, which can be a radiography system, a fluoroscopy system or a urography system, which comprises at least one emitter displacement unit and at least one detector displacement unit. The X-ray system can preferably be a robotic radiography system which comprises an emitter stand as the emitter displacement unit and a detector stand as the detector displacement unit. The emitter stand and/or the detector stand in particular can be ceiling-mounted, i.e. fastened to the room ceiling. The detector displacement unit can alternatively be provided in a patient support so that the X-ray detector can be displaced within or underneath the patient support substantially parallel to the table plane.

An embodiment of the method has the steps of selecting, of portion-wise recording and of generating.

At least one embodiment of the invention further relates to a medical X-ray system for carrying out a method, preferably according to an embodiment of the invention, comprising:

an X-ray source arranged on an emitter displacement unit and an X-ray detector with a detection area arranged on a detector displacement unit,
a selection unit for selecting the examination region,
a recording unit for step-wise recording of successive recording portions,
a control unit for moving the X-ray source and the X-ray detector along a recording direction,
a determining unit for determining a strip-shaped detection region within the detection area for a recording portion, and
a generating unit for generating an assembled X-ray recording from the recording portions.

At least one embodiment of the invention further relates to a computer program product with a computer program which can be loaded directly into a memory apparatus of a control apparatus of an X-ray system, having program portions in order to carry out all the steps of a method according to an embodiment of the invention when the computer program is executed in the control device of the X-ray system.

At least one embodiment of the invention further relates to a computer-readable medium on which program portions that can be read in and executed by a computer unit are stored, in order to carry out all the steps of a method according to at least one embodiment of the invention when the program portions are executed by the X-ray system.

At least one embodiment of the invention further relates to a method for making an X-ray recording of an examination region of an examination object with an X-ray system including an X-ray source arranged on an emitter displacement unit and an X-ray detector including a detection area, arranged on a detector displacement unit, the method comprising:

selecting the examination region;

portion-wise recording successive recording portions in relation to the examination region, the portion-wise recording including moving the X-ray source and the X-ray detector along a common recording direction, determining a strip-shaped detection region, within the detection area for the recording, by expanding an extent of the X-ray recording as compared with a further different X-ray recording recorded with a strip-shaped detection region parallel to an edge of the X-ray detector, and acquiring and recording each respective successive recording portion, of the successive recording portions, using the determined detection region and the X-ray source; and generating an assembled X-ray recording of the examination region from the successive recording portions recorded.

At least one embodiment of the invention further relates to a medical X-ray system, comprising:

an X-ray source, arranged on an emitter displacement unit and an X-ray detector including a detection area arranged on a detector displacement unit;

a selection unit to select an examination region;

a recording unit to record, in a step-wise manner, successive recording portions;

a control unit to move the X-ray source and the X-ray detector along a recording direction;

a determining unit to determine a strip-shaped detection region within the detection area, for a recording portion; and a generating unit to generate an assembled X-ray recording from the successive recording portions recorded.

At least one embodiment of the invention further relates to a non-transitory computer program product storing a computer program, directly loadable into a memory apparatus of a control apparatus of an X-ray system, including program portions to carry out the method of an embodiment when the computer program is executed in the control apparatus of the X-ray system.

At least one embodiment of the invention further relates to a non-transitory computer-readable medium storing program portions, configured to be read in and executed by a computer unit, to carry out the method of an embodiment when the program portions are executed by the X-ray system.

BRIEF DESCRIPTION OF THE DRAWINGS

Example embodiments of the invention will now be described in more detail, making reference to the drawings. In the drawings.

DETAILED DESCRIPTION OF THE EXAMPLE EMBODIMENTS

Figure 1:
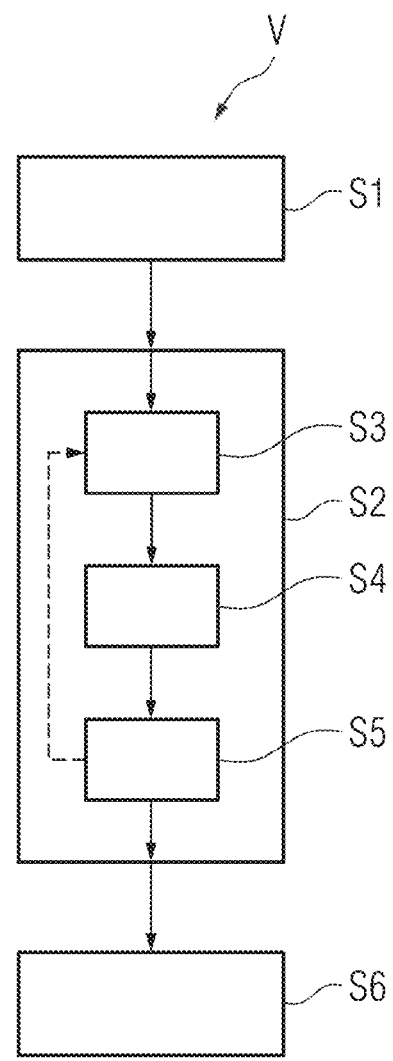
FIG. 1 shows a method in a first embodiment according to an embodiment of the invention, in a schematic representation.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for making a, particularly two-dimensional, X-ray recording of an examination region of an examination object with an X-ray system which comprises an X-ray source arranged on an emitter displacement unit and an X-ray detector with a detection area arranged on a detector displacement unit. The X-ray source can emit, in particular, X-ray radiation in the direction of the X-ray detector. The examination object is arranged between the X-ray source and the X-ray detector.

At least one embodiment of the invention relates to an X-ray system, which can be a radiography system, a fluoroscopy system or a urography system, which comprises at least one emitter displacement unit and at least one detector displacement unit. The X-ray system can preferably be a robotic radiography system which comprises an emitter stand as the emitter displacement unit and a detector stand as the detector displacement unit. The emitter stand and/or the detector stand in particular can be ceiling-mounted, i.e. fastened to the room ceiling. The detector displacement unit can alternatively be provided in a patient support so that the X-ray detector can be displaced within or underneath the patient support substantially parallel to the table plane.

An embodiment of the method has the steps of selecting, of portion-wise recording and of generating.

In the step of selecting, the examination region is selected. The selection can take place, for example, manually via a user interface, in particular, by the user. Alternatively or additionally, the selection can take place automatically. As the basis for selection, for the manual and/or automatic selection, for example, a camera image of the examination object or a light field projected onto the examination object can be used.

In the step of portion-wise recording, successive recording portions are recorded in relation to the examination region. The totality of the recording portions comprises the examination region. The successive recording portions are recorded for recording the selected examination region. The successive recording portions can follow one another, in particular, temporally and spatially. The X-ray recording can map a substantially unmoving examination object or, typically, no dynamic changes are investigated in the examination object in the context of the X-ray examination. Adjacent recording portions can, in particular, at least partially overlap. The examination region is subdivided or partitioned, in particular, into recording portions.

The step of portion-wise recording thereby comprises the steps of moving, determining and acquiring. In this way, the examination region can be recorded substantially completely portion-wise. For each recording portion, a portion dataset is generated. The step of portion-wise recording can comprise, in particular, a performance of the steps of moving, determining and acquiring, in each case for recording or acquiring a recording portion. In particular, a repetition loop with the following steps can be provided: moving, determining and thereby adjusting the strip-shaped detection region and subsequent acquisition of the recording portion.

Thereby, a first sequence can comprise the steps, in the following order, of: moving, determining and acquiring. Alternatively, a second sequence can comprise the steps, in the following order, of: determining, moving and acquiring. Further alternatively, the steps of moving and determining can take place at least partially simultaneously. Yet further alternatively, the determination of a plurality of recording portions or detection regions can take place before the steps of moving and acquiring the plurality of recording portions take place.

In an example embodiment to be described in detail below, specifically the formation of a detection region along a diagonal of the detection area, for a plurality of recording portions, the detection region determined can be the same. The determined detection region of a first recording portion can thus remain the same for a second recording portion. A renewed determination and adjustment can possibly be dispensed with.

In the step of moving, the X-ray source and the X-ray detector are moved along a common recording direction. The movement velocity of the X-ray source and of the X-ray detector can be substantially the same. Alternatively, the movement velocity of the X-ray source and of the X-ray detector can be different. The movement velocity of the X-ray source and of the X-ray detector can be substantially the same within an examination or recording for a first subregion of the examination region and can be different for a second subregion of the examination region.

In the step of determining, an, in particular active, strip-shaped detection region within the detection area is determined for the recording portion such that an extent of the X-ray recording is expanded as compared with a further X-ray recording that is different therefrom recorded with a predetermined, strip-shaped detection region parallel to an edge of the X-ray detector.

The determined strip-shaped detection region has a determined position within the detection area. The detection area can comprise a matrix-shaped arrangement of a large number of detector pixels. The matrix-shaped arrangement can comprise a large number of rows and columns, each of a plurality of detector pixels. The detection area can be configured, in particular, as rectangular or square. The detection area can have a size, for example, of 42 cm×41.5 cm. The strip-shaped detection region can comprise, in particular, a plurality of, in particular, substantially complete rows of detector pixels. At least, in particular, the strip-shaped detection region can be active. The entire detection region can be active. In the step of acquisition, for example, the data of the entire detection area can be read out or only the data of the detection region can be read out. The portion dataset can comprise the data of the entire detection area or only the data of the detection region. In the step of generating, for example, only the data of the detection region of the associated recording portion can be used.

The extent of the X-ray recording or of the examination region is expanded or enlarged. The examination region can be, in particular, larger than a further examination region of a further X-ray recording with an unchangeable strip-shaped detection region, within the detection area, parallel to an edge of the X-ray detector. The predetermined, strip-shaped detection region parallel to an edge of the X-ray detector for making the further X-ray recording is substantially unchangeable for all recording portions. The predetermined detection region parallel to an edge of the X-ray detector can also be designated constant or fixed or as the sole detection region. In this case, on recording of the further examination region, substantially every recording portion is recorded with substantially the same detection region. As a result thereof, the bright-burn effect can be caused. The different further X-ray recording of the further examination region by way of the predetermined, strip-shaped detection region is typically not included in the method according to the invention. The different further X-ray recording can be used for comparison of the size of the recordable examination region. The further X-ray recording can differ from the X-ray recording, in particular, in that the examination region of the X-ray recording is expanded relative to the further X-ray recording with the further examination region. The further X-ray recording can differ, in particular, in that in the further X-ray recording, the detection region is predetermined, i.e. it remains unchanging from recording portion to recording portion and the detection region is formed parallel to one edge of the X-ray detector or of the detection region. The further X-ray recording can be included, in particular, by a known method.

The, in particular active, detection region has a first extent and a second extent. The first extent substantially corresponds to the width or the diagonal of the detection area. The second extent is smaller than the length or the height of the X-ray detector or the detection area. The second extent can be, for example, between 3 cm and 7 cm. Preferably, the second extent can amount to approximately 5 cm. The second extent can be between 5 and 20 percent of the height of the X-ray detector or of the detection area, in particular, 10 to 14 percent, preferably approximately 12 percent.

In the step of acquiring, the recording portion is acquired by way of the determined detection region and the X-ray source. In particular, a portion dataset can be generated and/or acquired. The X-ray source emits, in particular, X-ray radiation in the direction of the X-ray detector and the examination object arranged therebetween. The X-ray radiation not attenuated by the examination object is incident upon the detection region and is registered there. The X-ray radiation registered by the X-ray detector is stored and/or acquired in a portion dataset.

In the step of generating, an assembled X-ray recording of the examination region is generated from the recording portions. The image recording region or the X-ray recording is assembled from a plurality of sequentially recorded strip-shaped individual recordings or recording portions. The recording portions can overlap, in particular, at least slightly, so that for example, an assembly is simplified. The recording portions can overlap, in particular, at least slightly, so that for example, a location in the examination region is included in a plurality of recording portions. Thereby, data from a plurality of recording portions can contribute to a data point or pixel in the assembled X-ray recording. In particular, 3 or more recording portions can contribute to a data point and/or pixel in the assembled X-ray recording.

Advantageously, a so-called slot-scan can be recorded with a radiography system without it having to be amended mechanically therefor. Advantageously, the height of the overall image or of the assembled X-ray recording and/or of the examination region can be enlarged, in contrast to a use of a specified or predetermined or constant active detection region parallel to an edge of the X-ray detector. Advantageously, for example, the width of the image recording region or of the examination region can be enlarged.

An alternative, complex solution would be to adapt the mechanism of the X-ray system, such as for example, to use an X-ray detector the size of which is optimized for the slot-scan technique. This would have to have a shape which corresponds to the slot and/or the detection region, but such a detector would then however be usable exclusively for slot-scan recordings. This disadvantage is overcome by the method according to the invention.

According to one embodiment of the invention, in the step of determining, the detection region is displaced in the recording direction within the detection area relative to a preceding detection region of a preceding recording portion.

The method is configured for making an X-ray recording of an examination region of an examination object with an X-ray system. The X-ray system comprises an X-ray source arranged on an emitter displacement unit and an X-ray detector, with a detection area, arranged on a detector displacement unit. The method has the step of selecting the examination region. The method further has the step of portion-wise recording of successive recording portions in relation to the examination region, thereby comprising the steps of moving, determining and acquiring. In the step of moving, the X-ray source and the X-ray detector are moved along a common recording direction. In the step of determining, a strip-shaped detection region is displaced within the detection area for the recording portion, so that the detection region within the detection area can be displaced in the recording direction relative to a preceding detection region of a preceding recording portion. Thus an extent of the X-ray recording can be expanded as compared with a further X-ray recording different therefrom with a predetermined strip-shaped detection region parallel to an edge of the X-ray detector, wherein the predetermined, strip-shaped detection region for the recording portion and a preceding recording portion is constant or unchanging. In the step of acquiring, the recording portion is acquired by way of the determined detection region and the X-ray source. In the step of generating, an assembled X-ray recording of the examination region is generated from the recording portions.

The detection region can be adapted, in particular, to the examination region in which the detection region is displaced so that an expanded examination region can be recorded. The position of the detection region within the detection area can thereby be altered such that the center of gravity of the detection region changes in the recording direction relative to a preceding detection region or recording portion. The altered detection region can have an overlap, in particular, as compared with the preceding detection region. The altered detection region can have, for example, partially the same detection pixels and a portion of other detector pixels, in particular, arranged in the recording direction as compared with the preceding detection region, as the preceding detection region. Advantageously, the examination region can be expanded.

Advantageously, the image height of the X-ray recording and/or of the examination region can be maximized. The method can be designated a so-called shifting slot method. The detection region can become displaced during the X-ray recording.

In radiography systems, in particular robotic radiography systems, the travel range can be more severely restricted in recordings of standing and also of lying examination objects by the detector stand and/or the detector displacement unit than by the tube stand and/or the tube displacement unit.

In particular, the travel range in standing examination objects can be restricted downwardly by the X-ray detector and/or by the X-ray source. Thereby, the examination region can be restricted downwardly, in particular if the X-ray source is aligned centrally to the X-ray detector for a plurality of recording portions or all recording portions. By way of the method according to the invention, with the variable detection region within the detection area, the examination region can be expanded downwardly.

In the case of the upward travel range, the situation is similar and here also the region can be restricted by the detector stand, in particular, if the X-ray source is aligned centrally to the X-ray detector for a plurality or all of the recording portions. By way of the method according to the invention, with the variable detection region within the detection area, the examination region can be expanded upwardly in that the detection region is moved during the X-ray recording from below upwardly over the detector.

Advantageously, in the case of standing examination objects, for example, approximately 20 cm of additional image height can be gained and/or the examination region can be expanded along the recording direction.

In the case of an examination object arranged on a patient support, the travel range can also be restricted by the detector stand or the detector displacement unit, since the movement of the X-ray detector can be restricted, for example, by a table foot. By way of the method according to an embodiment of the invention, with the variable detection region within the detection area, the examination region can be expanded to the side in that the detection region is moved or displaced within the detection area during the X-ray recording.

According to one embodiment of the invention, in the step of moving, a detector movement velocity of the X-ray detector is lower than an emitter movement velocity of the X-ray source. In the step of moving, the X-ray source can, in particular, cover a greater distance in the same time as compared with the X-ray detector. Advantageously, the examination region and/or the X-ray recording can be expanded.

According to one embodiment of the invention, an extent of the X-ray recording along the recording direction is greater than the maximum spacing between the detector center in a start position of the X-ray detector and the detector center in an end position of the X-ray detector. The detector center can be configured, for example, in the center of gravity of the detection area. The detector center can also be designated the detector center position. An extent of the examination region along the recording direction can be greater than the maximum spacing between the detector center in a start position of the X-ray detector and the detector center in an end position of the X-ray detector. The X-ray recording maps the, in particular expanded, examination region.

The height of the overall image or of the recording region can thus be configured as large as possible with the given mechanical conditions of the X-ray system. For example, whole body recordings with a larger height or length range can advantageously be enabled.

According to one embodiment of the invention, an irradiation time and/or an irradiation amount is substantially homogenously distributed over the detection area. Over the duration of the X-ray recording, the X-ray radiation can be distributed spatially over the detection area. The loading of the X-ray detector can thus be homogenized. Advantageously, as even or homogenous a dose burden or illumination as possible can be achieved by X-ray radiation of substantially the whole detection area. Advantageously, the so-called bright-burn effect can be reduced and/or prevented.

The bright-burn effect can advantageously be prevented since during the scan or the X-ray recording, the whole detector portion or the whole detection region is not irradiated continuously. The radiation can be distributed homogeneously over the whole detection area.

According to one embodiment of the invention, in the step of determining, the detection region is imaged along a diagonal of the detection area. The method is configured for making an X-ray recording of an examination region of an examination object with an X-ray system. The X-ray system comprises an X-ray source arranged on an emitter displacement unit and an X-ray detector, with a detection area, arranged on a detector displacement unit. The method has the step of selecting the examination region. The method further has the step of portion-wise recording of successive recording portions in relation to the examination region, thereby comprising the steps of moving, determining and acquiring. In the step of moving, the X-ray source and the X-ray detector are moved along a common recording direction. In the step of determining, a strip-shaped detection region can be determined within the detection area for the recording portion such that the detection region can be imaged along a diagonal of the detection area. Thus an extent of the X-ray recording can be expanded as compared with a further X-ray recording different therefrom with a predetermined strip-shaped detection region parallel to an edge of the X-ray detector. In the step of acquiring, the recording portion is acquired by way of the determined detection region and the X-ray source. In the step of generating, an assembled X-ray recording of the examination region is generated from the recording portions.

Advantageously, a maximization of the slot width or a maximization of the extent of the X-ray recording can be achieved via a rotated X-ray detector. The X-ray detector can thereby be rotated about the axis of the surface normals of the detection area, such that a diagonal of the detection area is aligned substantially perpendicularly to the recording direction.

The embodiment of the detection region along a diagonal of the detection area can be used or reserved for a plurality of, in particular successive, recording portions. Thereby, the detection region can be determined for each recording portion. Alternatively, for a first recording portion, the detection region can be determined and the steps of moving and acquiring can each be carried out for each recording portion with this detection region.

In order to maximize the image width, the slot or the detection region can be mapped or configured on the rotated X-ray detector. The detection region can be configured, in particular, along the diagonal of the detection area and/or of the X-ray detector.

In particular in the case of a robotic radiography system, the X-ray detector can be rotated so that a detection region can be configured along the diagonal of the detection area. In particular for anterior-posterior/AP X-ray recording, the X-ray detector can be rotated via the detector stand or via a tilting unit or a rotatable mounting provided on the detector stand in mechanical connection with the detector stand. The X-ray detector and thus the detection area can be rotated about the surface normals of the detection area. With an X-ray detector of approximately 42×42 cm$^2$ in size, a maximum slot width of a maximum width or a maximum extent of the detection region of approximately 59 cm can result.

An, in particular robotic, radiography system can have a detector width and/or an extent of the detection area of, for example, approximately 42 cm. In the case of an X-ray focus to X-ray detector spacing of, for example 132 cm and an X-ray focus to examination object spacing of, for example, 105 cm, this results in an image width in the object of approximately 33.4 cm if the detection area is arranged such that an edge of the detection surface extends parallel to the recording direction and a further edge perpendicular thereto extends perpendicularly to the recording direction. This alignment of the detection area can be designated the standard alignment. The detection area can have an angle of substantially 0 degrees in relation to the recording direction.

In a rotated alignment wherein the diagonal of the detection area is aligned substantially perpendicularly to the recording direction, the detection area can have an angle of substantially 45 degrees, in particular, if the detection area is configured substantially square. With an X-ray detector of approximately 42×42 cm$^2$ in size, this results in a maximum slot width and/or a diagonal of the detection area with a length of approximately 59 cm. At a detector width or an extent of the detection area of, for example, approximately 42 cm, and at an X-ray focus to X-ray detector spacing of, for example, 132 cm and an X-ray focus to examination object spacing of, for example, 105 cm this results in an image width in the object of approximately 47 cm. At a slot height or an extent of the detection region along the recording direction of approximately 5 cm, a usable slot width and/or a usable image width in the examination object perpendicular to the recording direction of approximately 43 cm can result. Advantageously, the extent of the detection region perpendicularly to the recording direction can be expanded and/or enlarged. Advantageously, the usable image width in the examination object can be expanded.

In a special embodiment, in the step of determining, the detection region formed along the diagonal can be displaced in the recording direction within the detection area relative to a preceding detection region of a preceding recording portion. For example, a more homogeneous radiation exposure or dose burden can thereby be enabled. The range of the displacement along the recording direction can be restricted in that the extent of the detection region perpendicularly to the recording direction is not smaller than the width of the detection area in a standard alignment.

According to one embodiment of the invention, an extent of the X-ray recording perpendicular to the recording direction is greater than a detector width of the X-ray detector. In the step of determining, the detection region can be configured along a diagonal of the detection area. The extent of the examination region, in particular, in the plane of the detection area, perpendicular to the recording direction can be greater than a detector width of the X-ray detector in a normal position or a standard alignment, wherein in the standard alignment, the at least one edge of the detection area is aligned parallel to the recording direction. The extent of the X-ray recording perpendicular to the recording direction and the detector width of the X-ray detector and/or of the detection area can lie, in particular, in the same plane, specifically the plane defined by the detection area. Advantageously, the X-ray recording can be expanded so that broader regions in the examination object can be mapped. For example, broader hip recordings can be enabled.

In further embodiments, recording portions with a detection region along a diagonal of the detection area and, in particular successive, recording portions, wherein the detection region is displaced from a recording portion to the subsequent recording portion within the detection area or wherein alternatively a predetermined detection region is set or determined. Both methods for expanding the X-ray recording can advantageously be combined.

With a rotated X-ray detector, the travel range of the X-ray detector can be restricted. A broad image field can be necessary, primarily in the trunk region, in particular hips and shoulders. At the legs and the head, a narrower image field can be sufficient. Therefore, in the lower subregion of the examination region, for example, in the region of the feet, recording can be performed portion-wise with the moving detection region. The detection region for the first recording portion can be formed, in particular, substantially on the lower edge of the detection area and parallel to an edge of the X-ray detector. For the subsequent recording portions, the detection region can travel along the recording direction, for example, as far as the region before the hips. Substantially in this position, the X-ray detector can be rotated so that the detection region is formed along the diagonals of the detection region. A plurality of recording portions can now be recorded and/or acquired with the detection region along the diagonals of the detection region, for example, comprising the region of the hips and possibly the shoulders. In the region above the shoulders, the X-ray detector can be rotated at one position so that the detection region is formed parallel to an edge of the X-ray detector. A plurality of recording portions can now be recorded, wherein the detection region is displaced along the recording direction, in particular, substantially as far as the upper edge of the X-ray detector. Advantageously, the examination region can be broadened or elongated in regions. Overall, the examination region can be expanded, in particular, as compared with an X-ray recording which uses only a predetermined detection region.

According to one embodiment of the invention, in the step of portion-wise determining, for a first recording portion, a first detection region is determined along a diagonal of the detection area, and for a second recording portion, a second detection region is determined parallel to an edge of the X-ray detector which is arranged perpendicular to the recording portion.

Advantageously, firstly an expanded or broader region of the examination region can be recorded and thereafter, a region of usual width.

According to one embodiment of the invention, furthermore, in the step of portion-wise recording, for a third recording portion, a third detection region is displaced in the recording direction within the detection area relative to the second detection region. Advantageously, the region of usual width can be elongated or expanded by displacement of the detection region along the recording direction from the second recording portion to the third recording portion.

According to one embodiment of the invention, in the step of portion-wise recording:
for a first recording portion, a first detection region is determined parallel to an edge of the X-ray detector which edge is arranged perpendicular to the recording direction, and
for a second recording portion, a second detection region within the detection area is displaced in the recording direction relative to the first detection region.

Advantageously, the region of usual width can be elongated or expanded by displacing the detection region along the recording direction from recording portion to recording portion.

According to one embodiment of the invention, furthermore, in the step of portion-wise recording, furthermore, for a third recording portion, a third detection region is determined along a diagonal of the detection area. Advantageously, firstly a region of usual width and subsequently an expanded or broader region of the examination region can be recorded.

According to one embodiment of the invention, the examination object is arranged standing between the X-ray source and the X-ray detector or the examination object is arranged lying on a patient support between the X-ray source and the X-ray detector.

At least one embodiment of the invention further relates to a medical X-ray system for carrying out a method, preferably according to an embodiment of the invention, comprising:
an X-ray source arranged on an emitter displacement unit and an X-ray detector with a detection area arranged on a detector displacement unit,
a selection unit for selecting the examination region,
a recording unit for step-wise recording of successive recording portions,
a control unit for moving the X-ray source and the X-ray detector along a recording direction,
a determining unit for determining a strip-shaped detection region within the detection area for a recording portion, and
a generating unit for generating an assembled X-ray recording from the recording portions.

The, in particular medical, X-ray system is configured for making an X-ray recording of an examination region of an examination object. The X-ray system has an X-ray source arranged on an emitter displacement unit and an X-ray detector with a detection area arranged on a detector displacement unit. The medical device can be, in particular, a robotic radiography system. The step of moving can be carried out via the emitter displacement unit and/or the detector displacement unit. The X-ray source and the X-ray detector are moved along a common recording direction. The control unit is configured to move the X-ray source and the X-ray detector along a recording direction. The control unit can, in particular, move the emitter displacement unit and/or the detector displacement unit.

The selection unit can comprise, for example, a user interface for selecting the examination region. For example, a screen for display and an input device for input based upon the display can be provided.

The recording unit is configured to record step-wise successive recording portions in relation to the examination region.

The determining unit is configured for determining a strip-shaped detection region within the detection area for a recording portion. The determining unit is configured, for example, in the form of a computer unit such that an extent of the X-ray recording is expanded, in particular, as compared with a further X-ray recording different therefrom with a predetermined strip-shaped detection region parallel to an edge of the X-ray detector.

The X-ray detector is configured to acquire the recording portion by way of the determined detection region. The X-ray detector and the X-ray source can be designated the acquisition unit. The generating unit is configured for generating an assembled X-ray recording from the recording portions. The generating unit can comprise a further computer unit and/or a processor. The generating unit can further comprise a storage unit for storing the recording portions and/or the assembled X-ray recording.

According to one embodiment of the invention, the X-ray detector comprises a rotatable mounting and/or a variable strip-shaped detection region.

The rotatable mounting can also be configured in the form of a tilt unit arranged on the detector stand and nevertheless still be comprised by the X-ray detector, for example, via a mechanical connection. The rotatable mounting and/or the tilt unit is configured in mechanical connection with the X-ray detector and with the detector stand and/or the detector displacement unit. The rotatable mounting and/or tilt unit enables a rotation of the X-ray detector through, in particular, at least approximately 45 degrees. Advantageously, the detection region can be formed along the diagonal of the detection area.

The variable strip-shaped detector region can be configured, for example, such that all the detector pixels are read out, but in particular only the data of the data pixels in the strip-shaped detector region are utilized for generating the assembled X-ray recording. The variable, strip-shaped detector region can be set and/or selected by way of selective data selection from the portion datasets. For example, a parameter set which defines which detector pixels are to be used when generating the assembled X-ray recording can be assigned to the portion dataset.

Alternatively, in particular only, the data pixels of the strip-shaped detector region can be read out and then utilized for generating the assembled X-ray recording. The variable strip-shaped detector region can be set by way of control, in particular for readout, of the X-ray detector. Advantageously, the strip-shaped detector region can be variably selected or specified.

Advantageously, a detector-side collimator can be dispensed with. A detector-side, in particular variable, collimator would require a constructional change of the X-ray detector and/or would again entail restrictions with regard to the travel range of the X-ray detector. Advantageously, an X-ray detector can be used which enables both areal individual recordings with the entire detection area and also a slot-scan method with an expanded examination region. Advantageously, a strip detector having a strip-shaped detection area substantially having the size of the strip-shaped detection region can be dispensed with.

At least one embodiment of the invention further relates to a computer program product with a computer program which can be loaded directly into a memory apparatus of a control apparatus of an X-ray system, having program portions in order to carry out all the steps of a method according to an embodiment of the invention when the computer program is executed in the control device of the X-ray system.

At least one embodiment of the invention further relates to a computer-readable medium on which program portions that can be read in and executed by a computer unit are stored, in order to carry out all the steps of a method according to at least one embodiment of the invention when the program portions are executed by the X-ray system.

FIG. 1 shows an example design of a method V according to the invention in a first embodiment in a schematic representation. The method V is configured for making an X-ray recording of an examination region of an examination object. The recording is carried out with an X-ray system which comprises an X-ray source arranged on an emitter displacement unit and an X-ray detector with a detection area arranged on a detector displacement unit. In one embodiment, the method can have the following steps.

In the step of selecting S1, the examination region of the examination object is selected. The examination region can, for example, also be designated the examination field. The examination region can comprise, for example, at least one of the following body regions of the examination object: legs, hips, trunk, shoulders and/or head. The examination region can be, for example, rectangular and/or can comprise a plurality of mutually adjacent rectangular regions.

In the step of portion-wise recording S2, successive recording portions are recorded in relation to the examination region. The examination region is recorded via a plurality of recording portions. A plurality of recording portions are assigned to the examination region. The recording portions are, in particular, adjacent and/or overlapping. The examination region is subdivided into a plurality of examination portions. During the portion-wise recording S2, the steps of moving S3, determining S4 and acquiring S5 are carried out. In a preferred embodiment, the steps of moving S3, determining S4 and acquiring S5 can be repeated in a loop (dashed path), in particular in order to acquire and/or record a recording portion in each case.

In the step of moving S3, the X-ray source and the X-ray detector are moved along a common recording direction. In the step of determining S4, a strip-shaped detection region within the detection area is determined for the recording portion such that an extent of the X-ray recording is expanded as compared with a further X-ray recording that is different therefrom recorded with a predetermined, strip-shaped detection region parallel to an edge of the X-ray detector. In the step of acquiring S5, the recording portion is acquired by way of the determined detection region and the X-ray source.

In particular, a large number of recording portions are acquired. The portion-wise recording enables, in particular, a large number of acquired recording portions. In the step of generating S6, an assembled X-ray recording of the examination region is generated from the recording portions.

Figure 2:
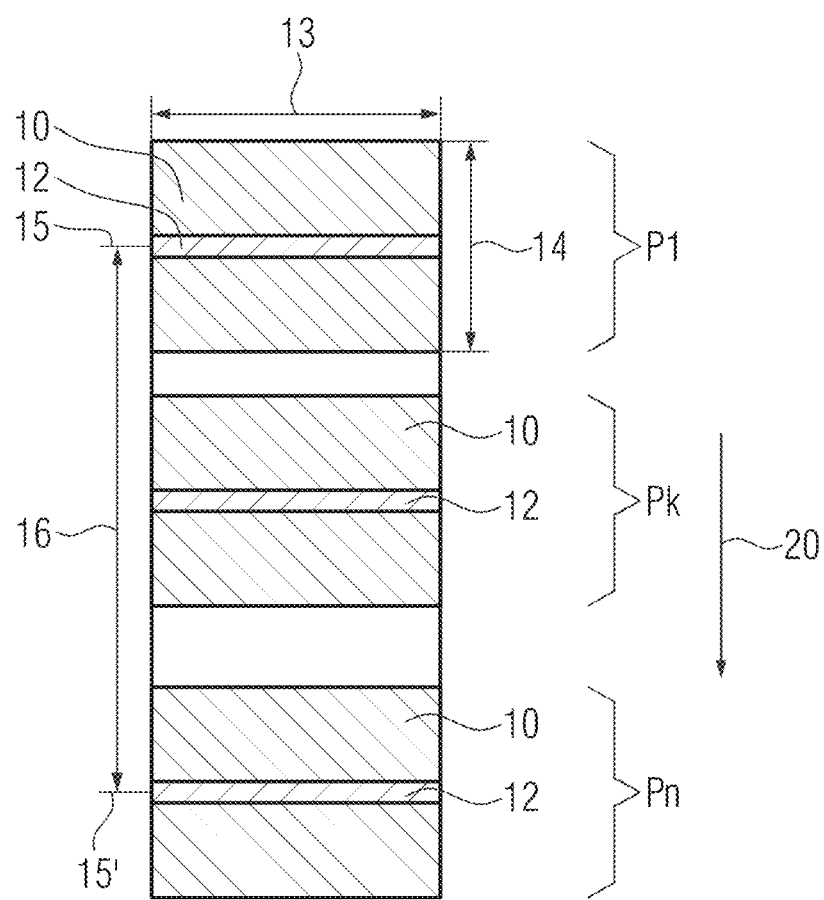
FIG. 2 shows a further method for making a further X-ray recording, in a schematic representation.

FIG. 2 shows an example further method for making a further X-ray recording in a schematic representation. The further X-ray recording is made with a predetermined strip-shaped detection region 12 parallel to an edge of the X-ray detector. The X-ray detector comprises the detection area 10. The predetermined strip-shaped detection region 12 is provided at a constant and/or predetermined position within the detection area 10, for example, centrally between the upper and lower edge of the detection area 10 and/or of the X-ray detector. The predetermined detection region 12 is configured as strip-shaped parallel to an edge of the X-ray detector and/or of the detection area 10. The detection area 10 has a detector width 13 and a detector height 14.

The X-ray detector having the detection area 10 and the X-ray source move along the recording direction 20 from a start position P1 to a further position Pk and an end position Pn. In a start position P1, in a further position Pk and in an end position Pn, the detection region 12 is provided at a constant and/or predetermined position within the detection area 10, for example, centrally between the upper and lower edge of the detection area 10 and/or of the X-ray detector.

In a start position P1, the detection region is provided at a detector center position and/or at the detector center 15. In an end position Pn, the detection region is provided at a detector center position and/or the detector center 15'. The, in particular maximum, spacing 16 between the detector center position 15 in a start position P1 and the detector center position 15' in an end position is restricted, in particular, by the possible travel range of the X-ray source or of the X-ray detector. With this method, a further X-ray recording can be made.

Figure 3:
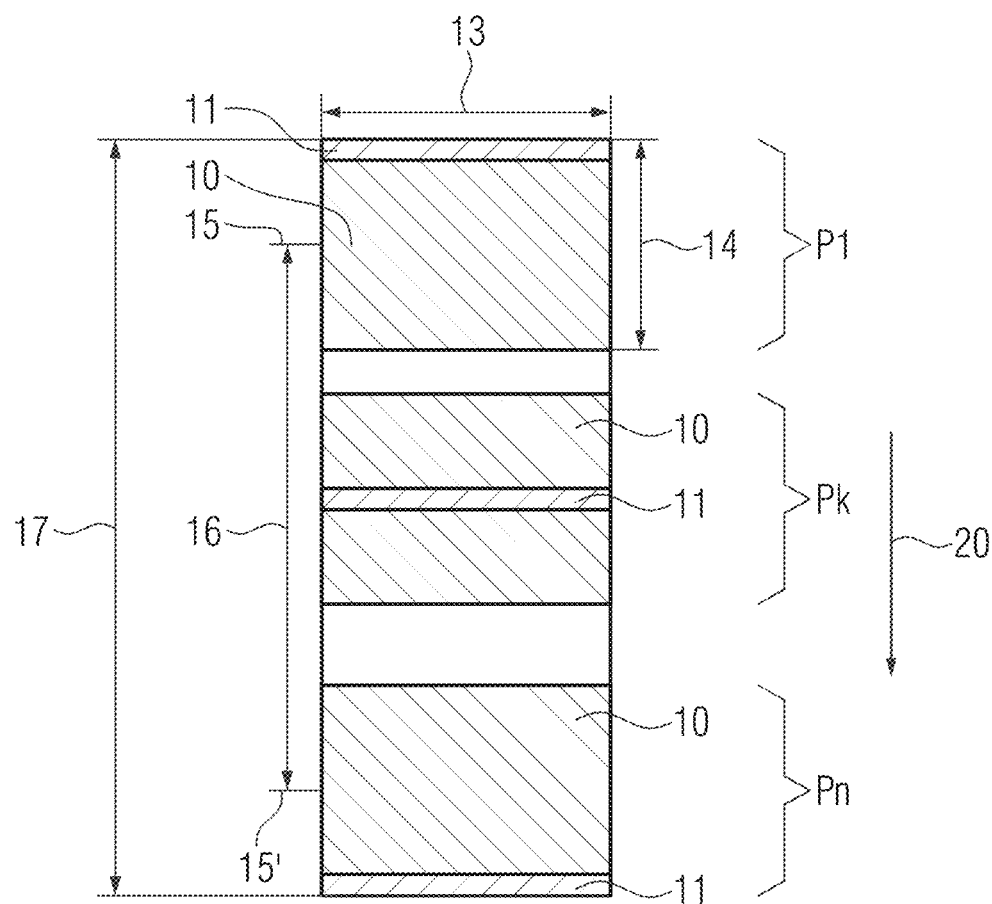
FIG. 3 shows a method in a second embodiment according to an embodiment of the invention, in a schematic representation.

FIG. 3 shows an example embodiment of a method V according to the invention in a second embodiment in a schematic representation. In the step of determining, the detection region 11 is displaced in the recording direction 20 within the detection area 10 for the recording in a further position Pk as compared with a preceding detection region of a preceding recording portion in a start position P1. In the step of determining, the detection region 11 is displaced in the recording direction 20 within the detection area 10 for the recording in an end position Pn relative to a preceding detection region of a preceding recording portion in a further position Pk. In the start position P1, the detection region 11 is provided at the upper edge of the detection area. In the further position Pk, the detection region 11 is provided at the detector center position and/or the detector center. At the end position Pn, the detection region 11 is provided at the lower edge of the detection region 10. In the step of moving, a detector movement velocity of the X-ray detector is lower than an emitter movement velocity of the X-ray source. The X-ray detector covers a smaller distance in the same time as compared with the X-ray source.

An extent of the X-ray recording 17 along the recording direction 20 is greater than the maximum spacing 16 between the detector center position in a start position P1 of the X-ray detector and the detector center position 15' in an end position Pn of the X-ray detector. The extent 17 of the X-ray recording is expanded as compared with a further X-ray recording different therefrom recorded with a predetermined strip-shaped detection region parallel to an edge of the X-ray detector. The irradiation time and/or the irradiation amount is substantially homogenously distributed over the detection area.

Figure 4:
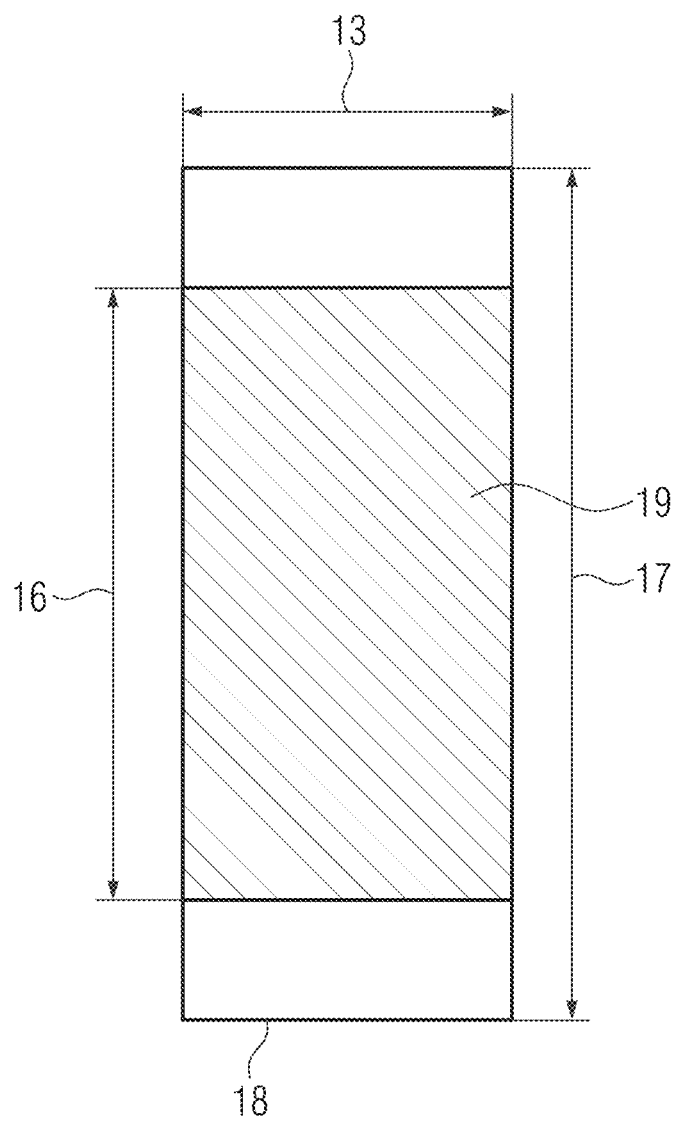
FIG. 4 shows an X-ray recording according to the invention in a first embodiment as compared with a further X-ray recording.

FIG. 4 shows an example X-ray recording 18 according to the invention in accordance with a first embodiment as compared with a further X-ray recording 19. The extent 17 of the X-ray recording 18 is expanded as compared with a further X-ray recording 19 different therefrom recorded with a predetermined strip-shaped detection region parallel to an edge of the X-ray detector. The extent of the further X-ray recording parallel to the extent 17 corresponds to the spacing 16. The X-ray recording 18 comprises a rectangular area defined by the detector width 13 and the extent of the X-ray recording 17. The further X-ray recording 19 comprises a rectangular area defined by the detector width 13 and the maximum spacing 16.

Figure 5:
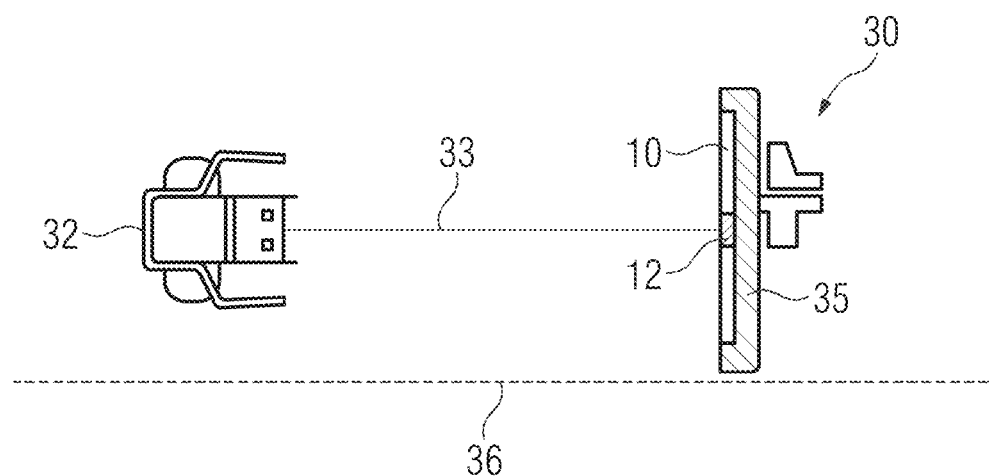
FIG. 5 shows an arrangement of the X-ray system, in a first embodiment, for making a further X-ray recording.

FIG. 5 shows an example arrangement of the X-ray system in a first embodiment for making a further X-ray recording. The medical X-ray system 30 comprises an X-ray source 32 and an X-ray detector 35. The X-ray source 32 emits X-ray radiation 33 in the direction of the X-ray detector 35. The X-ray source 32 and the X-ray detector 35 are associated with one another such that the central beam of the X-ray source is incident substantially perpendicularly on the detection area 10, in particular, on the detection region 12. The (room) floor is a movement limit 36 of the X-ray detector 35, whereby the travel range of the X-ray detector 35 is limited. The arrangement is suitable, in particular, for recording standing patients and/or examination objects. The detection region 12 is provided at the detector center position.

Figure 6:
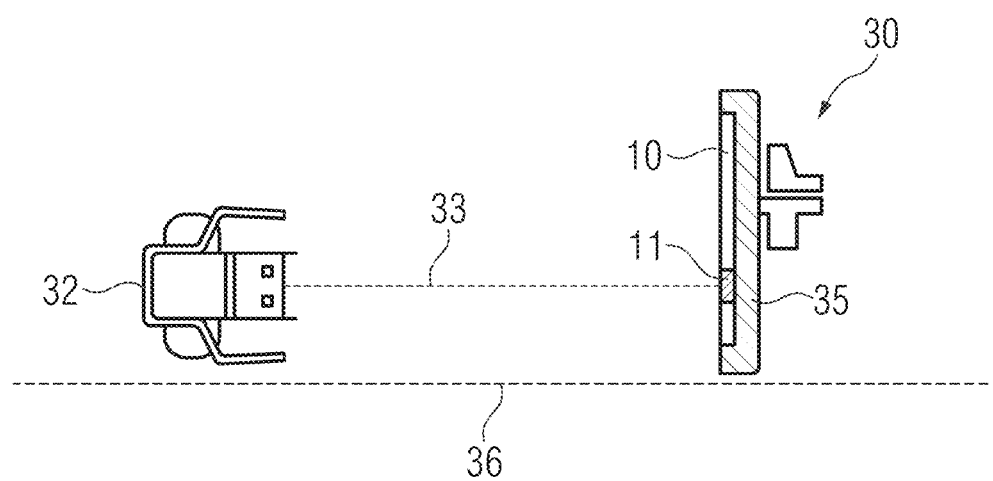
FIG. 6 shows an arrangement according to the invention of the X-ray system according to the invention, in a first embodiment, for making an X-ray recording according to an embodiment of the invention.

FIG. 6 shows an example arrangement according to the invention of the X-ray system according to the invention in a first embodiment for making an X-ray recording according to the invention. The X-ray source 32 and the X-ray detector 35 are associated with one another such that the central beam of the X-ray source is incident substantially perpendicularly on the detection area 10, in particular, on the detection region 11.

The (room) floor is a movement limit 36 of the X-ray detector 35, whereby the travel range of the X-ray detector 35 is limited. The (room) floor is also a movement limit 36 of the X-ray source 32, whereby the travel range of the X-ray source 32 is limited. The arrangement is suitable, in particular, for recording standing patients and/or examination objects. The detection region 11 is provided underneath the detector center position. The X-ray source 32 and the X-ray detector 35 are in an end position. Thereby, the extent of the X-ray recording can be expanded.

Figure 7:
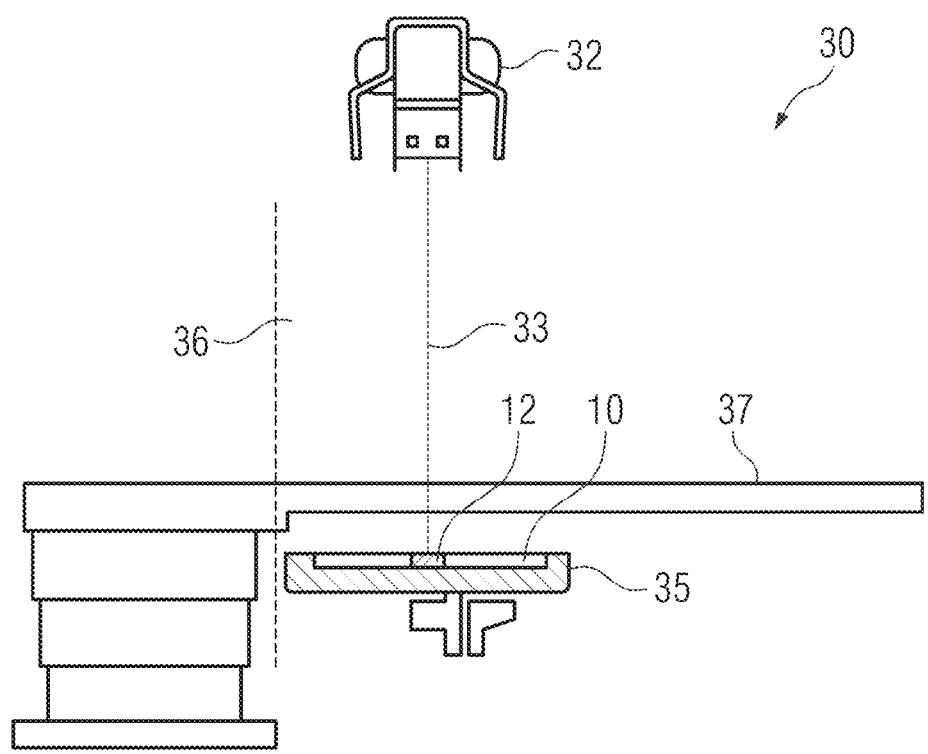
FIG. 7 shows an arrangement of the X-ray system in a second embodiment for making a further X-ray recording.

FIG. 7 shows an example arrangement of the X-ray system according to the invention in a second embodiment for making a further X-ray recording. The patient table 37, in particular, its foot is a movement limit 36 of the X-ray detector 35, whereby the travel range of the X-ray detector 35 is limited. The arrangement is suitable, in particular, for recording a lying patient and/or examination object lying on the patient table 37. The detection region 12 is configured at the detector center position.

Figure 8:
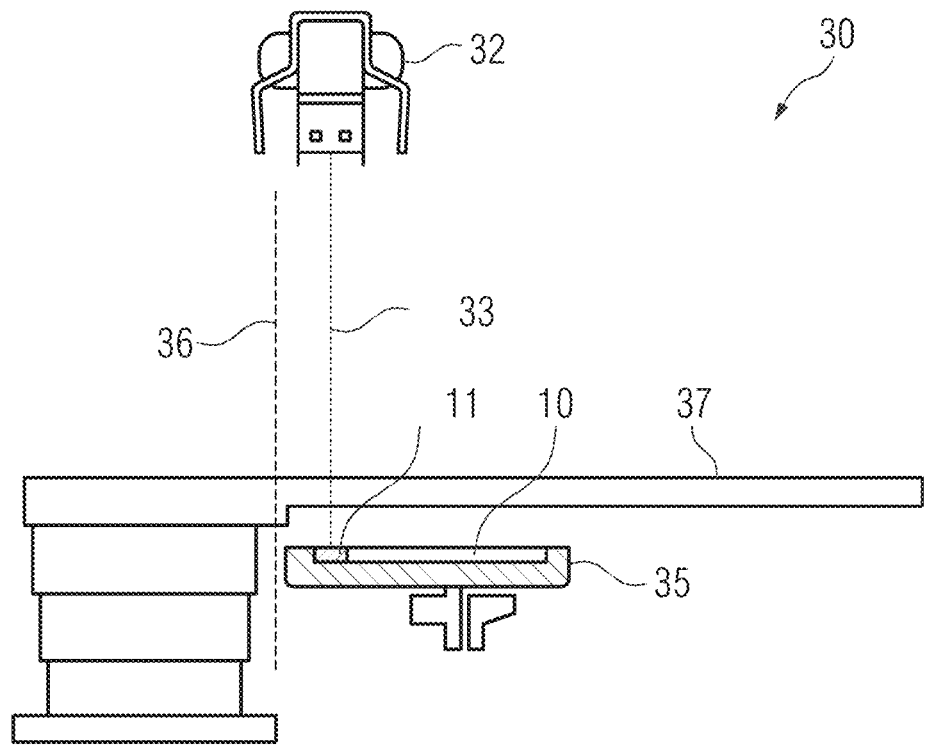
FIG. 8 shows an arrangement according to the invention of the X-ray system according to an embodiment of the invention, in a second embodiment, for making an X-ray recording according to an embodiment of the invention.

FIG. 8 shows an example arrangement according to the invention of the X-ray system according to the invention in a second embodiment for making an X-ray recording according to the invention. The patient table 37 is a movement limit 36 of the X-ray detector 35, whereby the travel range of the X-ray detector 35 is limited. The arrangement is suitable, in particular, for recording lying patients and/or examination objects. The detection region 11 is formed to the left side of the detector center position or closer to the table foot as compared with the predetermined detection region 12 in FIG. 7. The X-ray source 32 and the X-ray detector 35 are in an end position. Thereby, the extent of the X-ray recording can be expanded.

Figure 9:
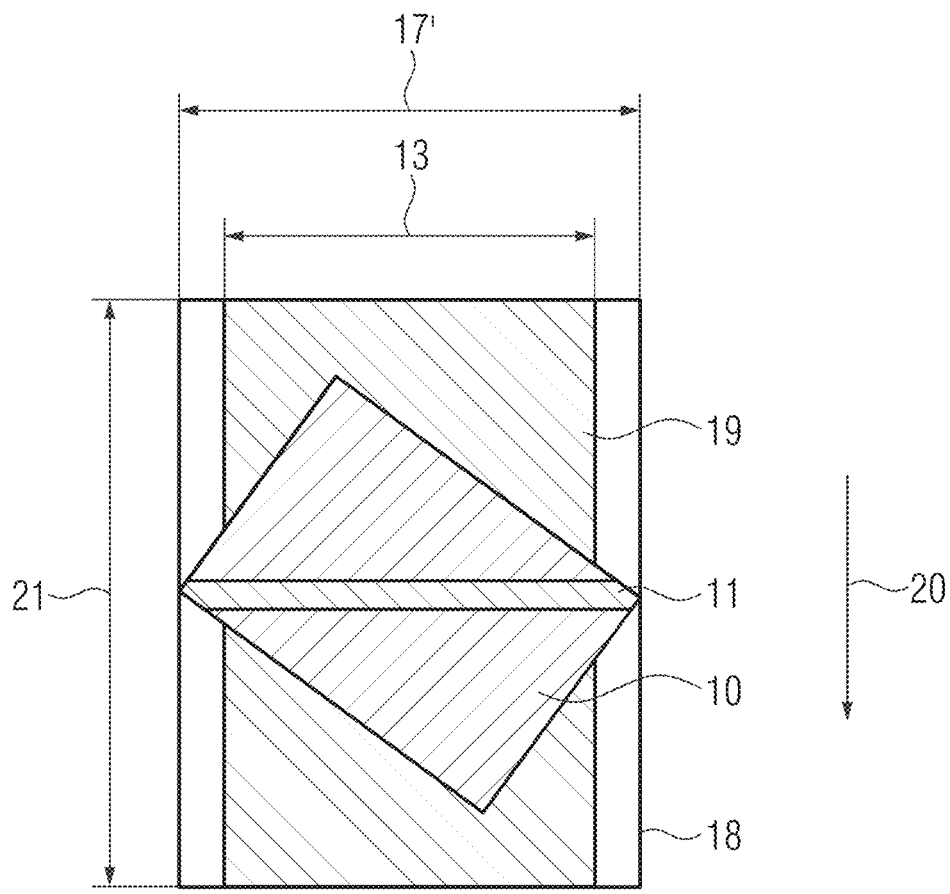
FIG. 9 shows an X-ray recording according to the invention, according to a second embodiment, as compared with a further X-ray recording.

FIG. 9 shows an example X-ray recording 18 according to the invention in a second embodiment as compared with a further X-ray recording 19. In the step of determining the detection region 11, the detection region 11 is imaged along a diagonal of the detection area 10. The detection region 11 moves with the X-ray detector along the recording direction 20, so that the examination region is recorded along the further extent 21. Thereby, an extent 17' of the X-ray recording 18 perpendicularly to the recording direction is greater than a detector width 13 of the X-ray detector.

The X-ray recording 18 comprises a rectangular area defined by the extent of the X-ray recording 17' and the further extent of the X-ray recording 21. The extent 17' substantially corresponds to the width of the detection region 11. The further X-ray recording 19 comprises a rectangular area defined by the detector width 13 and the maximum spacing or the further extent of the X-ray recording 21.

Figure 10:
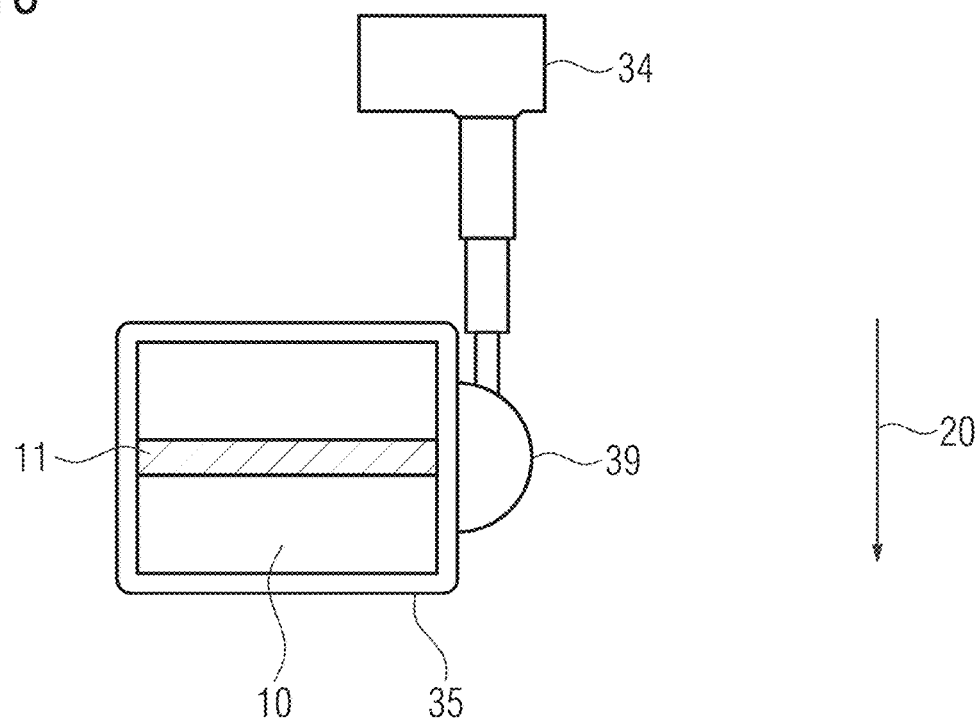
FIG. 10 shows a detector displacement unit according to an embodiment of the invention with an X-ray detector according to the invention having a detection region, in a first embodiment.

FIG. 10 shows an example detector displacement unit 34 with an X-ray detector 35 according to the invention having a detection region 11 in a first embodiment. The detection region 11 is configured as strip-shaped, preferably in a variable manner, within the detection area 10. The detector displacement unit 34 is preferably configured as an, in particular, ceiling-suspended detector stand. The mechanical connection between the X-ray detector 35 and the detector displacement unit 34 comprises a tilt unit 39 by which the X-ray detector 35 can be rotated and/or aligned. The X-ray detector 35 is rotated and/or aligned such that the detection region 11 is aligned perpendicularly to the recording direction 20.

Figure 11:
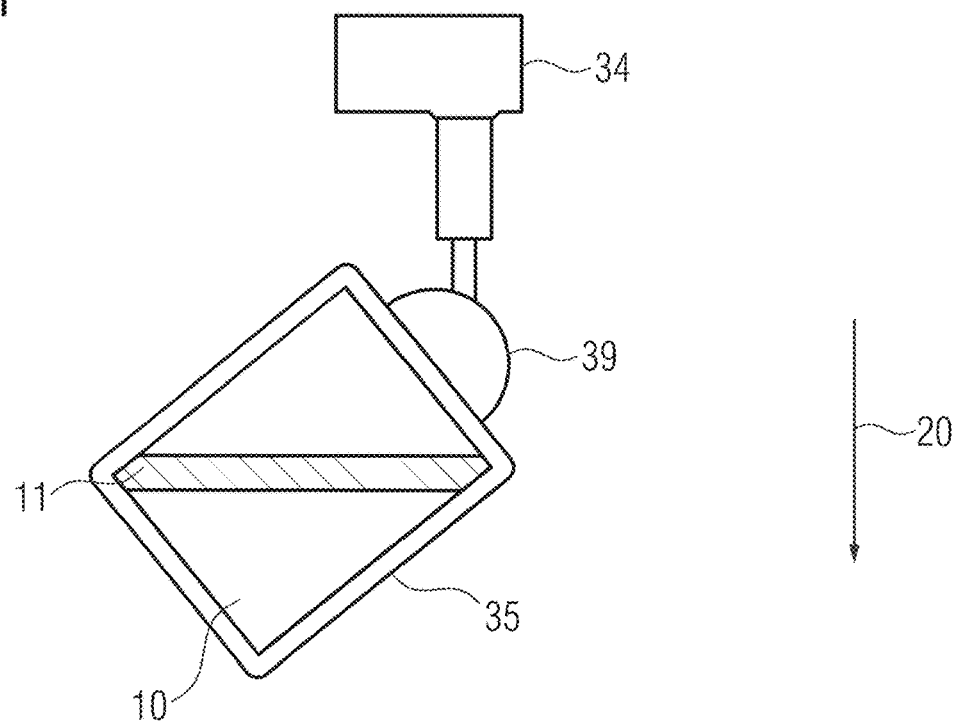
FIG. 11 shows a detector displacement unit according to an embodiment of the invention with an X-ray detector according to the invention having a detection region, in a second embodiment.

FIG. 11 shows an example detector displacement unit 34 with an X-ray detector 35 according to the invention having a detection region 11 in a second embodiment. The detection region 11 is configured as strip-shaped within the detection area 10 along the diagonal of the detection area 10. The detector displacement unit 34 is preferably configured as a detector stand. The mechanical connection between the X-ray detector 35 and the detector displacement unit 34 comprises a tilt unit 39. The X-ray detector 35 is tilted such that the detection region 11 is aligned perpendicularly to the recording direction 20.

Figure 12:
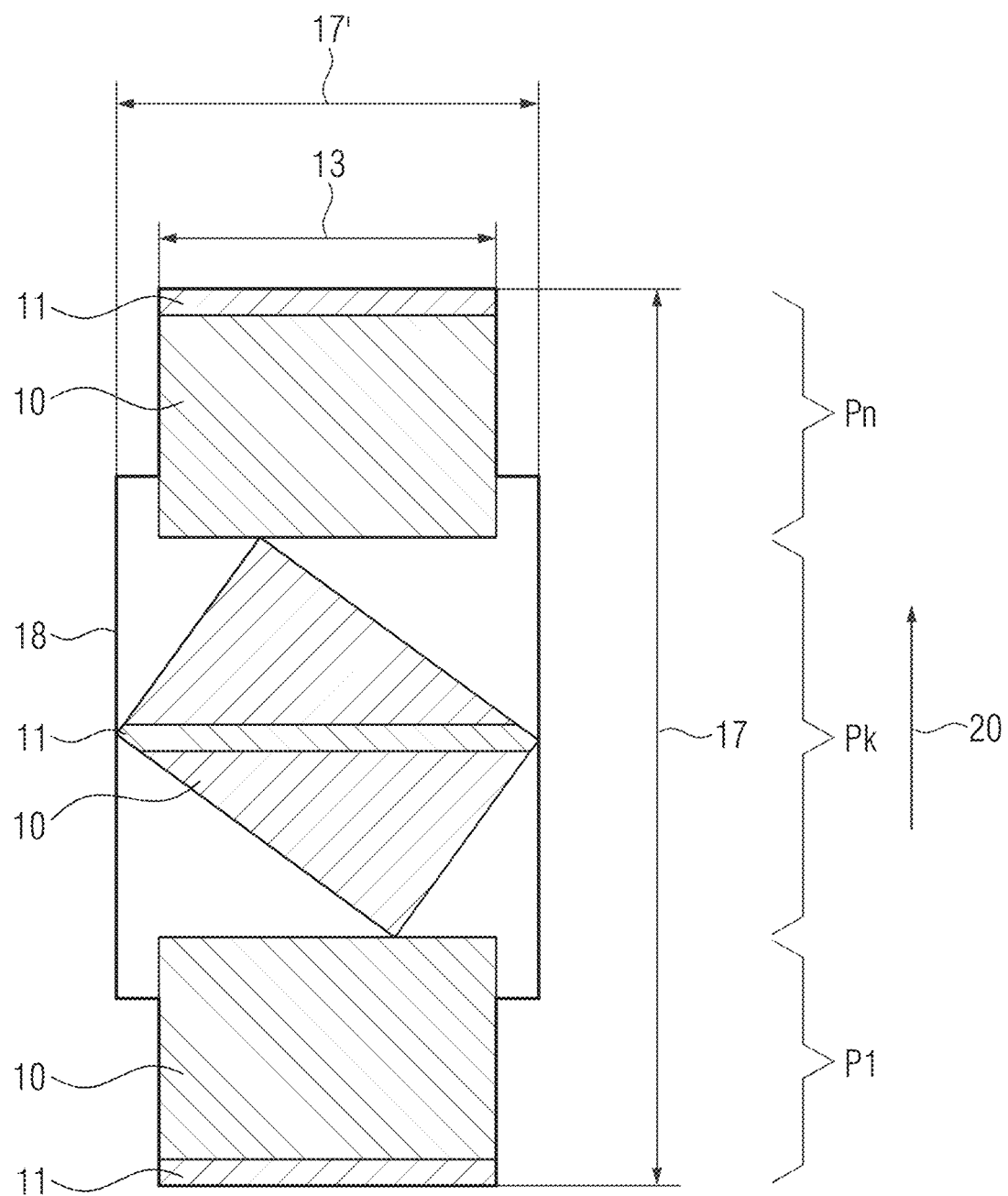
FIG. 12 shows a method according to the invention in a schematic representation, in a third embodiment.

FIG. 12 shows an example method according to the invention in a third embodiment in a schematic representation. In the step of portion-wise recording, embodiments described above are combined in an example manner. For a first recording portion, for example, in a start position P1, a first detection region 11 is determined parallel to an edge of the X-ray detector which is arranged perpendicularly to the recording direction 20. For example, the detection region 11 can be arranged at the lower edge of the X-ray detector. For a second recording portion, a second detection region is displaced in the recording direction within the detection area 10 relative to the first detection region. Subsequently, for a third recording portion, a third detection region 11 is determined along a diagonal of the detection area, for example in a further position Pk. For a fourth recording portion, a fourth detection region 11 is determined parallel to an edge of the X-ray detector which edge is arranged perpendicularly to the recording direction 20, for example, in an end position Pn. The detection region 11 is displaced in the recording direction 20 relative to a previous recording portion.

Figure 13:
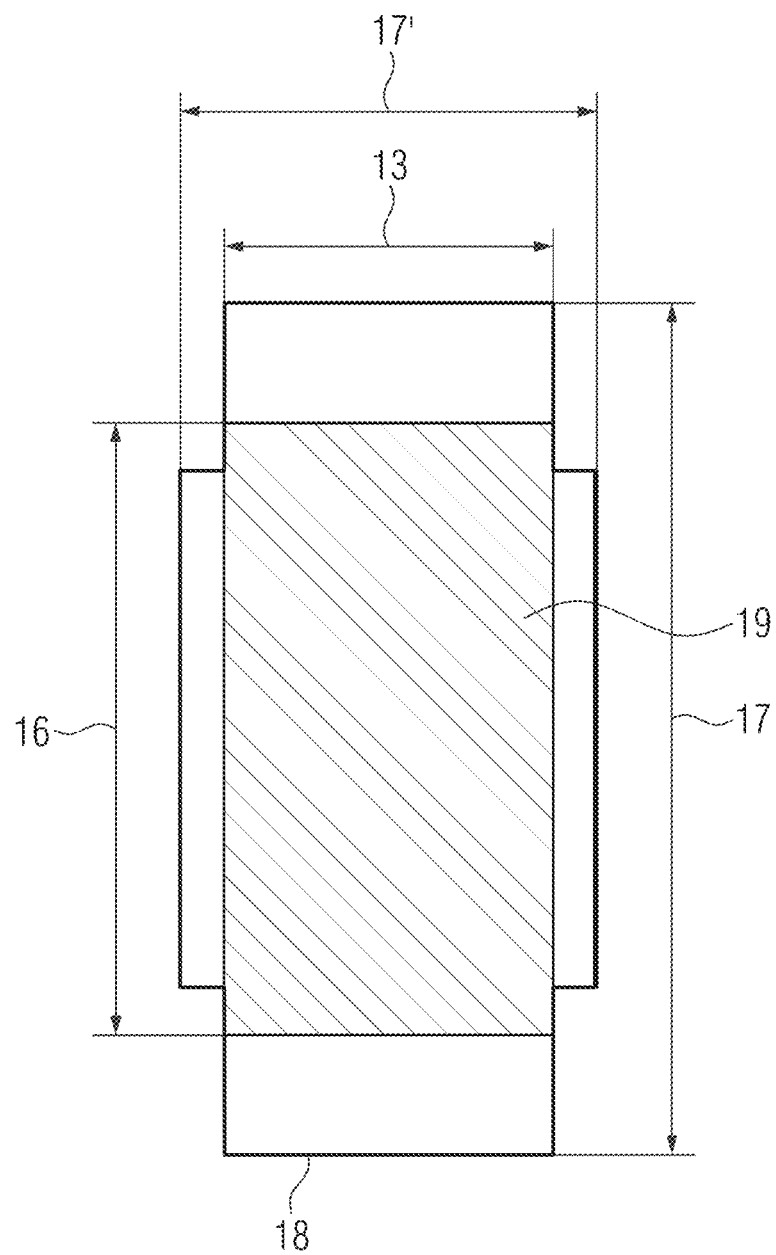
FIG. 13 shows an X-ray recording according to the invention in a third embodiment, as compared with a further X-ray recording.

FIG. 13 shows an example X-ray recording 18 according to the invention in a third embodiment as compared with a further X-ray recording 19. The X-ray recording 18 is defined along the extent 17 in the direction of the recording direction. Perpendicular thereto, the X-ray recording 18 is defined along the detector width 13 in a lower region and an upper region. In a central region, the X-ray recording 18 is defined along the extent 17'. The further X-ray recording 19 is rectangular and is defined by the detector width 13 and the spacing 16. The X-ray recording 18 is expanded as compared with the further X-ray recording 19 in the recording direction and in a central region perpendicularly to the recording direction.

Figure 14:
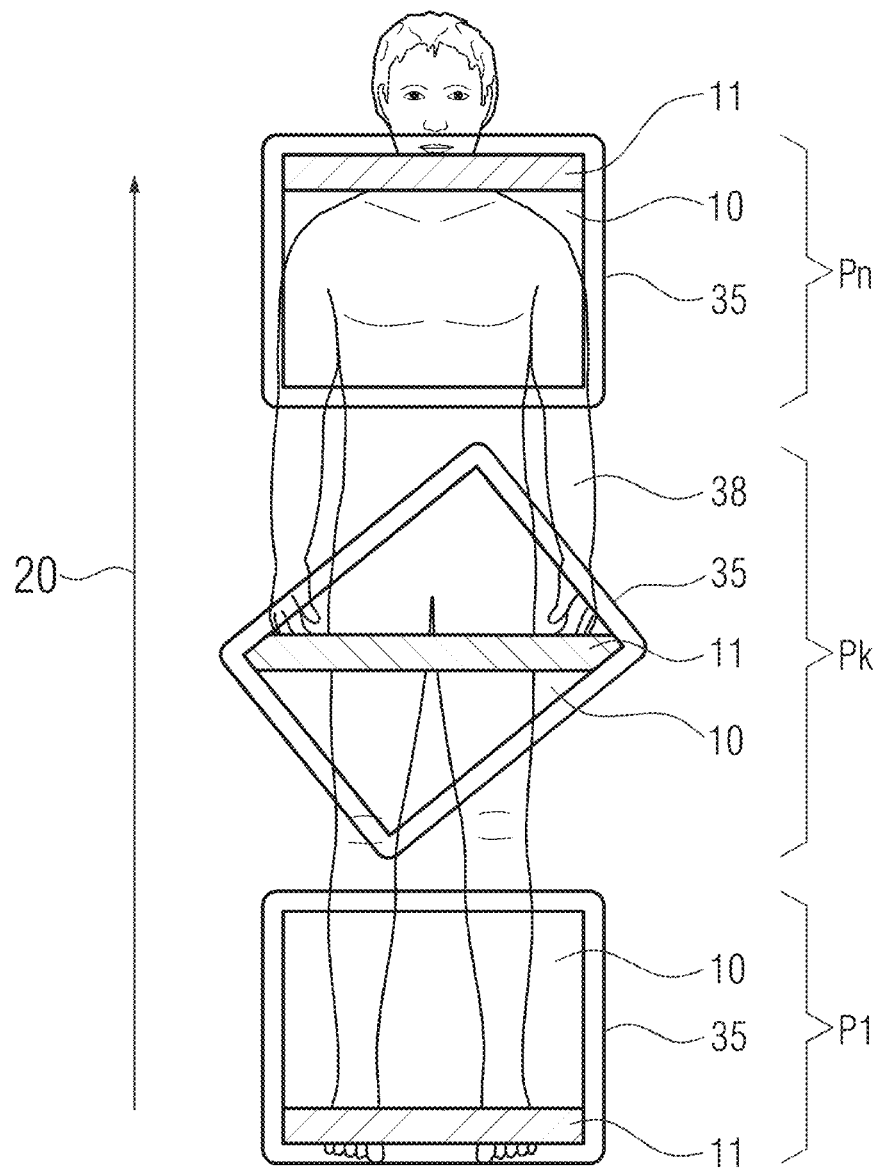
FIG. 14 shows a method according to the invention in a fourth embodiment, in a schematic representation.

FIG. 14 shows an example method according to the invention in a fourth embodiment, in a schematic representation. The fourth embodiment substantially corresponds to the third embodiment in FIG. 12. The respective position of the X-ray detector 35 is shown in relation to the examination object 38, by way of example, in the start position P1, the further position Pk and the end position Pn.

Figure 15:
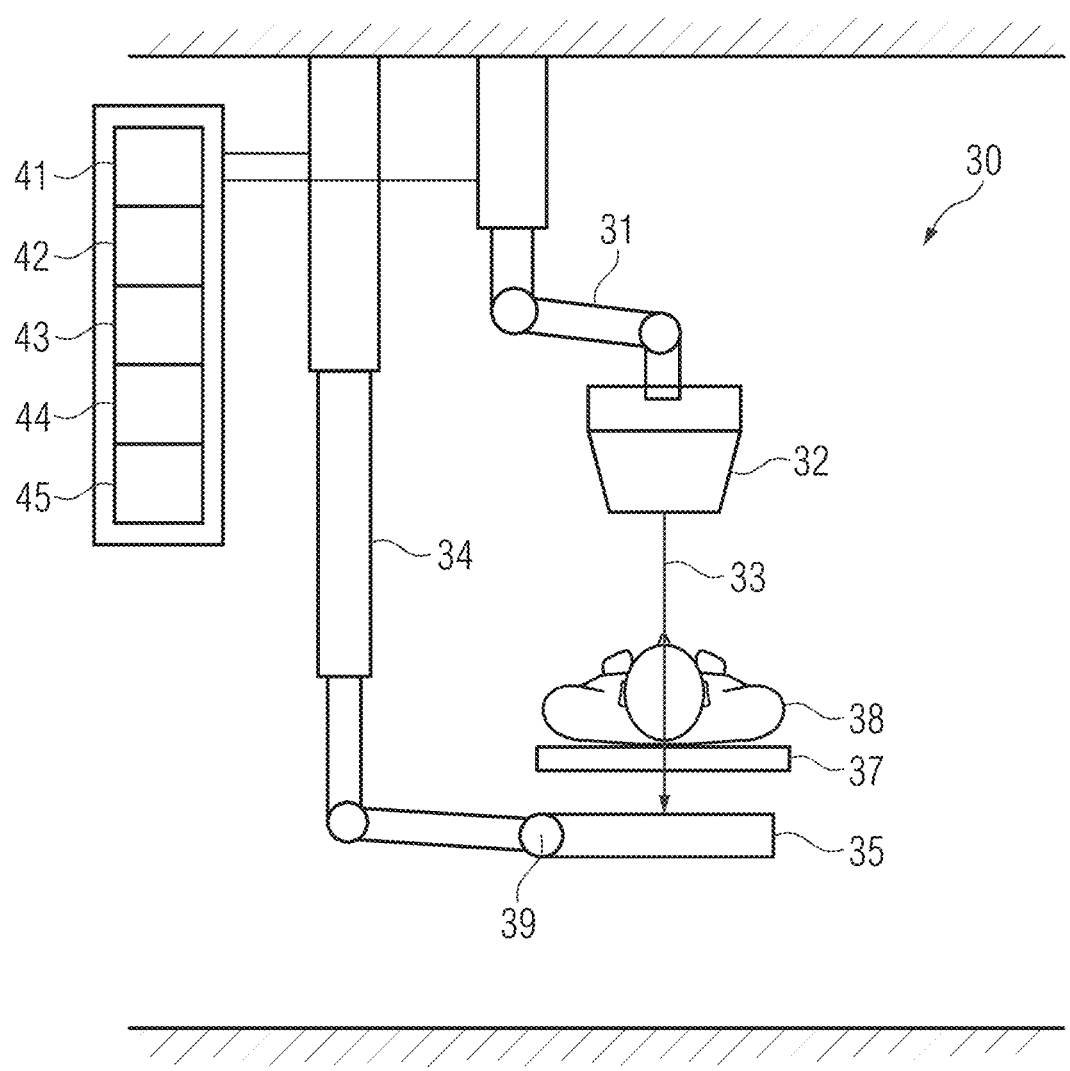
FIG. 15 shows an X-ray system according to an embodiment of the invention.

FIG. 15 shows an example medical X-ray system 30 according to the invention for carrying out a method according to the invention. The X-ray system 30 has an X-ray source 32 arranged on an emitter displacement unit 31 and/or an emitter stand and an X-ray detector 35 with a detection area arranged on a detector displacement unit 34 and/or a detector stand. The X-ray system 30 also has a selection unit 41 for selecting the examination region. The X-ray system 30 further has a recording unit 42 for step-wise recording of successive recording portions. The X-ray system 30 further has a control unit 43 for moving the X-ray source 32 and the X-ray detector 35 along a recording direction. The X-ray system 30 further has a determining unit 44 for determining a strip-shaped detection region within the detection area for a recording portion. The X-ray system 30 further has a generating unit 45 for generating an assembled X-ray recording from the recording portions. The X-ray detector 35 has a rotatable mounting, for example, in the form of a tilt unit 39 and/or a variable, strip-shaped detection region.

Although the invention has been described in detail with the preferred example embodiment, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for making an X-ray recording of an examination region of an examination object with an X-ray system including an X-ray source on an emitter displacement unit and an X-ray detector including a detection area on a detector displacement unit, the method comprising:
   selecting the examination region;
   portion-wise recording successive recording portions of the examination region, the portion-wise recording including,
      moving the X-ray source and the X-ray detector along a recording direction,
      determining a respective strip-shaped detection region of the detection area for each of the successive recording portions, the respective strip-shaped detection regions being determined such that at least one of the respective strip-shaped detection regions is along a diagonal of the detection area, and
      acquiring and recording each of the successive recording portions using the respective strip-shaped detection region and the X-ray source; and
   generating an assembled X-ray recording of the examination region from the successive recording portions recorded.

2. The method of claim 1, wherein the determining includes,
   displacing the respective strip-shaped detection region for a first recording portion of the successive recording portions, the respective strip-shaped detection region for the first recording portion being displaced in the recording direction relative to the respective strip-shaped detection region for a second recording portion of the successive recording portions, the first recording portion being preceded by the second recording portion.

3. The method or claim 1, wherein
   the respective strip-shaped detection region for a first recording portion of the successive recording portions is the at least one of the respective strip-shaped detection regions along the diagonal of the detection area, and
   the acquiring and recording of the first recording portion is along the diagonal of the detection area.

4. The method of claim 1, wherein
   the respective strip-shaped detection region for a first recording portion of the successive recording portions is the at least one of the respective strip-shaped detection regions along the diagonal of the detection area, and
   the respective strip-shaped detection region for a second recording portion of the successive recording portions is parallel to an edge of the detection area and perpendicular to the recording direction.

5. The method of claim 1, wherein
   the respective strip-shaped detection region for a first recording portion of the successive recording portions is parallel to an edge of the detection area and perpendicular to the recording direction, and
   the portion-wise recording includes displacing the respective strip-shaped detection region for a second recording portion of the successive recording portions, the respective strip-shaped detection region for the second recording portion being displaced in the recording direction relative to the respective strip-shaped detection region for the first recording portion.

6. A non-transitory computer-readable medium storing program portions, configured to be read in and executed by a computer unit, to carry out the method of claim 1 when the program portions are executed by the X-ray system.

7. The method of claim 2, wherein the moving includes,
moving the X-ray detector at a first velocity, and
moving the X-ray source at a second velocity, the first velocity being less than the second velocity.

8. The method of claim 2, wherein an extent of the X-ray recording along the recording direction is greater than a maximum distance between a center of the detection area in a start position of the X-ray detector and the center of the detection area in an end position of the X-ray detector.

9. The method of claim 2, wherein at least one of an irradiation time or an irradiation amount is substantially homogenously distributed over the detection area.

10. The method of claim 2, wherein
the respective strip-shaped detection region for the first recording portion is the at least one of the respective strip-shaped detection regions along the diagonal of the detection area, and
the acquiring the recording of the first recording portion is along the diagonal of the detection area.

11. The method of claim 2, wherein
the respective strip-shaped detection region for the first recording portion is the at least one of the respective strip-shaped detection regions being along the diagonal of the detection area, and
the respective strip-shaped detection region for the second recording portion is parallel to an edge of the X-ray detector and perpendicular to the recording direction.

12. The method of claim 2, wherein
the respective strip-shaped detection region for the second recording portion is parallel to an edge of the detection area and perpendicular to the recording direction.

13. The method of claim 7, wherein an extent of the X-ray recording along the recording direction is greater than a maximum distance between a center of the detection area in a start position of the X-ray detector; and the center of the detection area in an end position of the X-ray detector.

14. The method of claim 7, wherein at least one of an irradiation time or an irradiation amount is substantially homogenously distributed over the detection area.

15. The method of claim 3, wherein an extent of the X-ray recording perpendicular to the recording direction is greater than a width of the detection area.

16. The method of claim 4, wherein the portion-wise recording further includes,
displacing the respective strip-shaped detection region for a third recording portion of the successive recording portions, the respective strip-shaped detection region for the third recording portion being displaced in the recording direction relative to the respective strip-shaped detection region for the second recording portion.

17. A medical X-ray system, the medical X-ray system comprising:
an X-ray source on an emitter displacement unit and an X-ray detector on a detector displacement unit, the X-ray detector having a detection area;
a selection unit configured to select an examination region or an examination object;
a recording unit configured to portion-wise record successive recording portions of the examination region;
a control unit configured to move the X-ray source and the X-ray detector along a recording direction;
a determining unit configured to determine a respective strip-shaped detection region of the detection area for each of the successive recording portions, at least one of the respective strip-shaped detection regions being along a diagonal of the detection area; and
a generating unit configured to generate an assembled X-ray recording from the successive recording portions recorded.

18. The medical X-ray system of claim 17, wherein the X-ray detector includes at least one of a rotatable mount or a variable strip-shaped detection region.

19. A device for making an X-ray recording, the device comprising:
one or more processors; and
a memory storing computer-executable instructions that, when executed by one or more processors, causes the device to
select an examination region of an examination object;
record successive recording portions of the examination region,
determine a respective strip-shaped detection region of a detection area of an X-ray detector for each of the successive recording portions, at least one of the respective strip-shaped detection regions being along a diagonal of the detection area, and
generate an assembled X-ray recording from the successive recording portions recorded.

* * * * *